United States Patent
Cook et al.

(10) Patent No.: US 10,660,562 B2
(45) Date of Patent: May 26, 2020

(54) SYSTEM AND METHOD FOR MEASURING HAIR DIAMETER

(71) Applicant: Conopco, Inc., Englewood Cliffs, NJ (US)

(72) Inventors: Joanne Louise Cook, Wirral (GB); Myriam Fessi, Liverpool (GB); Morag Fiona Hutcheon, Cambridgeshire (GB); Justin Nobuyuki Minow Pinkney, Cambridge (GB); Robert Lindsay Treloar, Hoole (GB); Stephen Lee Wire, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 141 days.

(21) Appl. No.: 15/575,880

(22) PCT Filed: May 19, 2016

(86) PCT No.: PCT/EP2016/061345
§ 371 (c)(1),
(2) Date: Nov. 21, 2017

(87) PCT Pub. No.: WO2016/193018
PCT Pub. Date: Dec. 8, 2016

(65) Prior Publication Data
US 2018/0116583 A1    May 3, 2018

(30) Foreign Application Priority Data
May 29, 2015  (EP) .................................... 15169995

(51) Int. Cl.
*A61B 5/107*   (2006.01)
*A61B 5/00*    (2006.01)
(Continued)

(52) U.S. Cl.
CPC ............ *A61B 5/448* (2013.01); *A61B 5/1072* (2013.01); *A61B 5/1079* (2013.01);
(Continued)

(58) Field of Classification Search
CPC ....... A61B 5/448; A61B 5/107; A61B 5/1072; A61B 5/1079; A61B 5/1074; G01B 11/08
(Continued)

(56) References Cited

U.S. PATENT DOCUMENTS 5,164,793 A * 11/1992 Wolfersberger ....... A43D 1/025
    33/3 R
5,237,520 A *  8/1993 White .................... A43D 1/025
    12/142 N
(Continued)

FOREIGN PATENT DOCUMENTS

CN      1359006     7/2002
CN      1523323     8/2004
(Continued)

OTHER PUBLICATIONS

IPRP1 in PCTEP2016061345, dated Dec. 5, 2017.
(Continued)

*Primary Examiner* — Christopher W Fulton
(74) *Attorney, Agent, or Firm* — Foley & Lardner LLP

(57) ABSTRACT

A system for measuring the diameter of a human hair (50), the system comprising: a mobile device (20); and a reference card (10) including a hair attachment mechanism (11a, 11b); the mobile device configured to convert an image of a human hair attached to the reference card by the attachment mechanism into a measurement of the diameter of the human hair, using the size of the reference card itself and/or the size of a calibration marker (12) on a surface of the reference card as a size reference.

13 Claims, 7 Drawing Sheets

(51) Int. Cl.
  *G01B 11/08* (2006.01)
  *G06T 7/62* (2017.01)
(52) U.S. Cl.
  CPC ............ *A61B 5/6898* (2013.01); *G01B 11/08* (2013.01); *G06T 7/62* (2017.01); *A61B 5/0022* (2013.01); *A61B 2560/0233* (2013.01); *G06T 2207/30204* (2013.01)
(58) Field of Classification Search
  USPC .......................................... 33/512; 382/199
  See application file for complete search history.

(56) References Cited

U.S. PATENT DOCUMENTS

| | | | | |
|---|---|---|---|---|
| 5,689,446 | A | * | 11/1997 | Sundman ................ A43D 1/02 33/3 A |
| 6,546,356 | B1 | * | 4/2003 | Genest .................... A43D 1/02 702/153 |
| 7,051,452 | B2 | * | 5/2006 | Brooks ................... A43D 1/025 33/227 |
| 10,043,068 | B1 | * | 8/2018 | Hansen ............. G06K 9/00362 |
| 2004/0168329 | A1 | * | 9/2004 | Ishimaru ................. A43D 1/02 33/3 R |
| 2005/0097762 | A1 | * | 5/2005 | Biesbrouck .......... A61B 5/1036 33/3 R |
| 2012/0320191 | A1 | | 12/2012 | Meschkat et al. |
| 2014/0118521 | A1 | | 5/2014 | Conti et al. |
| 2015/0009312 | A1 | | 1/2015 | Verna et al. |
| 2015/0052008 | A1 | | 2/2015 | Campbell |
| 2015/0228084 | A1 | * | 8/2015 | Belyaev ................. A43D 1/025 382/199 |
| 2016/0286906 | A1 | * | 10/2016 | Malal ..................... G01C 11/02 |
| 2017/0169571 | A1 | * | 6/2017 | Hung ..................... A43D 1/025 |
| 2018/0035762 | A1 | * | 2/2018 | Towns ................... A43D 1/025 |
| 2018/0160777 | A1 | * | 6/2018 | Hei ........................ G06Q 30/06 |

FOREIGN PATENT DOCUMENTS

| | | |
|---|---|---|
| CN | 1679478 | 10/2005 |
| CN | 1795813 | 7/2006 |
| CN | 1821715 | 8/2006 |
| CN | 1933778 | 3/2007 |
| CN | 102102978 | 6/2011 |
| CN | 201867174 | 6/2011 |
| CN | 102165492 | 8/2011 |
| CN | 102494616 | 6/2012 |
| CN | 102519373 | 6/2012 |
| CN | 103063617 | 4/2013 |
| CN | 103499303 | 1/2014 |
| CN | 103608666 | 2/2014 |
| CN | 103829928 | 6/2014 |
| CN | 1267501 | 9/2019 |
| DE | 8030534 | 7/1981 |
| EP | 1210908 | 5/2002 |
| GB | 2384425 | 1/2005 |
| JP | H04073052 | 3/1992 |
| JP | 2002224086 | 8/2002 |
| JP | 2008241256 | 10/2008 |
| JP | 2013153408 | 8/2013 |
| JP | 2014500999 | 1/2014 |
| JP | 2014522500 | 9/2014 |
| KR | 1020140015780 | 2/2014 |
| KR | 1020150018973 | 2/2015 |
| KR | 101506685 | 3/2015 |
| WO | WO2012059851 | 5/2012 |
| WO | WO-2018109421 A1 * | 6/2018 ............ A43D 1/025 |

OTHER PUBLICATIONS

Search Report and Written Opinion in PCTEP2016061345, dated Jul. 27, 2016.
Search Report in EP15169995, dated Nov. 13, 2015.
Written Opinion in EP15169995, dated Nov. 13, 2015.
L'Oreal; https://play.google.com/store/apps/details?id=com.modiface.loreal.stylemyhair.
Schwarzkopf; http://www.schwarzkopf-professional.co.uk/skp/uk/en/home/products/colour/house-of-color.html.
Schwarzkopf; http://www.schwarzkopf-professional.co.uk/skp/uk/en/home/products/care/hair-expert-app.html.

* cited by examiner

Sobel X

Sobel Y

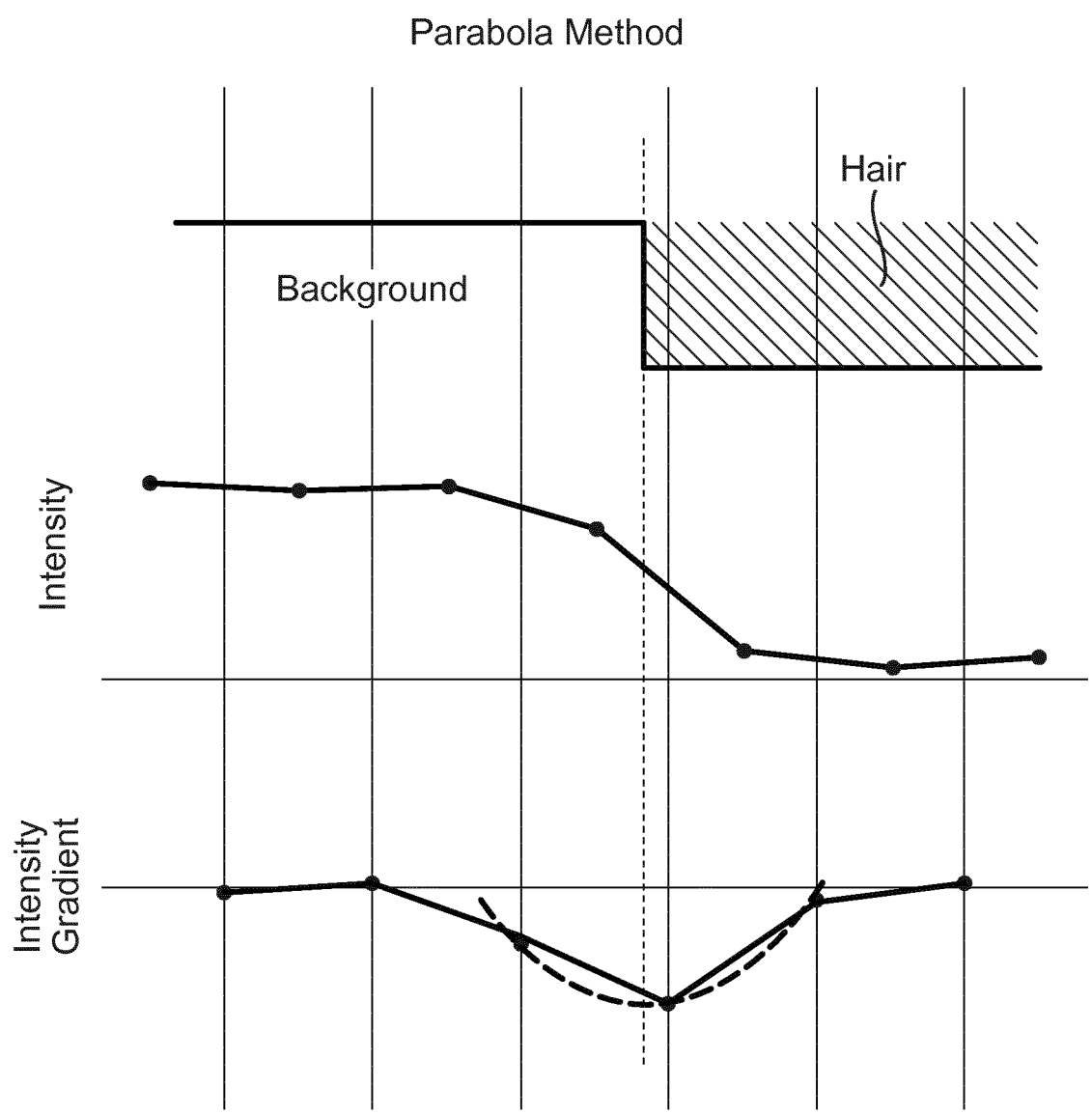

SYSTEM AND METHOD FOR MEASURING HAIR DIAMETER

CROSS-REFERENCE TO RELATED APPLICATIONS

This application claims priority to International Patent Application No. PCT/EP2016/061345, filed on May 19, 2016, and European Patent Application No. 15169995.6, filed on May 29, 2015, both of which are incorporated herein by reference in their entireties.

FIELD OF THE INVENTION

The present invention relates to a system and method for measuring the diameter of a human hair, more particularly to a system comprising a mobile device and a reference card.

BACKGROUND OF THE INVENTION

Consumers of hair products are able to select from a high volume of available products, due in part to the fact that many hair care brands have increasingly large product ranges.

These product ranges may cover various product categories including: shampoos, conditioners, treatments and styling products. Within each product category, a brand may produce multiple versions of a product with the ingredients of each version chosen to address the particular needs of a given target hair type. For example, a given hair type may include one or more of the following: thick hair, frizzy hair, thin hair, colour treated hair, and damaged hair.

Each version of a product could be clearly marketed for its target hair type. However, it may be difficult for a consumer to accurately identify what hair type they actually belong to and the vast array of choice could therefore lead to confusion. When a consumer chooses a version of a product, their choice is usually based on nothing more than their own perception of their hair type and this perception may be inaccurate particularly if it is based on external factors such as advertising or relative comparisons with friends and family. In addition, terms such as "thick hair" or "thin hair" can be open to misinterpretation. For example, a consumer may have many hair strands, but each hair strand may be of a thinner than average diameter.

In the current market, it is therefore easy for consumers to wrongly assign themselves a specific hair type and to select a specific version of a product, the ingredients of which may not be the best match for the actual characteristics of their hair. Such selection of a less than optimal product version can lead to poor customer satisfaction.

There is therefore a need for consumers of hair products to be able to make more accurate, more informed choices about what version of a haircare product is best for them.

SUMMARY OF THE INVENTION

The present invention aims to solve the above problems by providing a system for measuring the diameter of a human hair, the system comprising: a mobile device; and a reference card including a hair attachment mechanism; the mobile device configured to convert an image of a human hair attached to the reference card by the attachment mechanism into a measurement of the diameter of the human hair, using the size of the reference card itself and/or the size of a calibration marker on a surface of the reference card as a size reference.

In this way, the claimed system provides a mechanism for quantitative analysis of the hair upon which the choice of product can be based. By taking actual measurements, the consumer is more likely to choose the optimal product for their hair as errors which arise from qualitative descriptions of hair types can be prevented. The likelihood of customer satisfaction is therefore increased.

Advantageously, the system can be implemented by the user themselves at home and does not require any complicated or expensive laboratory equipment.

Optional features of the invention will now be set out. These are applicable singly or in any combination with any aspect of the invention.

The configuration of the mobile device to convert the image into a diameter measurement may take the form of a computer program product, tangibly embodied in a non-transitory computer readable medium, the computer program product including instructions for carrying out the steps required to turn the image taken by the digital imaging device into the diameter measurement.

For example, the computer program may be an app which is downloadable onto a mobile device.

The mobile device could be any electronic device such as: mobile phone/cellphone, tablet, phablet, laptop or a digital camera. The mobile device may comprise a digital imaging device (e.g. a camera) for capturing the image of the human hair attached to the reference card. In this way, the mobile device is configured to capture the image as well as to process it.

The surface of the reference card may be coloured white to make the colour contrast as great as possible between the hair to be measured and the card surface. A white surface would be particularly optimised for dark hairs (e.g. brown, black). For blond or grey hairs it may be preferable to include a dark surface to invert the colour contrast. A single reference card may be configured to be used with multiple hair colours by including a surface with a while background and a surface with a black background. White and black are used as examples, but could be substituted by other light or dark colours.

Optionally the reference card may contain instructions on its use or on the applications use.

Optionally, a surface of the reference card includes an adhesive region. Such an adhesive region would provide an additional attachment mechanism for attaching hair to the card which is particularly advantageous for the diameter measurement of curly hair because curly hair has an inherent resilience and may therefore more difficult to attach to the card using slits or a similar mechanism and once attached may not remain held in a fixed position.

Optionally the reference card has a matt surface. This surface may have a roughness more than or equal to the roughness of matt printer paper. This may correspond to a TAPPI 75 gloss value below 35%, even more preferably this may correspond to a TAPPI 75 gloss value of no more than 10%.

In this way, the amount of light absorbed by the card is increased. Reflections of light from the card are therefore minimised so that light spots in the image due to reflections of light sources are reduced. This is particularly important when the image is taken in artificial light. Bright spots in the image can affect the processing of the image so a matt surface of the reference card gives rise to a robust system that can be used in various lighting conditions or changing lighting conditions.

Where images are recorded in well-lit environments, it is particularly desirable for any flash on the mobile device to be disabled before an image is recorded. Where a flash might be useful (for example in an extremely poorly lit environment) the matt surface will help to minimise the effect of bright spots which arise as a result of the reflection of the flash.

The hair attachment mechanism may take the form of a first attachment point at one end of the card for receiving one end of the hair and a second attachment point at the opposite end of the card for receiving the other end of the hair.

In this way, one end of the hair can be placed in the attachment point at one end of the card, the hair can then be pulled taut before the other end of the hair is attached to the second attachment point. If the hair is held in a taut line between the first attachment point and the second attachment point, measurement across its diameter is facilitated, firstly because the hair is held still; the reduction in movement leading to a more reliable diameter measurement. Secondly, because the hair will be held in a given position, with its longitudinal axis aligned along a path defined by the shortest possible distance between the first attachment point and the second attachment point. In this way, by setting the longitudinal axis of the hair in a given position, the measurement of the diameter in a direction transverse to this longitudinal axis is facilitated.

Optionally, one or more of the attachment points may be a slit in the card.

Optionally, both the first attachment point and the second attachment point may take the form of a slit in an edge of the reference card.

The hair attachment means could take other forms including a clip at each end, an adhesive point at each end, a protrusion/rod at each end around which a hair could be wrapped.

The mobile device may be configured to present the image taken by the digital imaging device to the user for quality verification before processing the image. In this way, the quality of the digital image is checked by the user before a diameter measurement is calculated. This provides a quick mechanism for eliminating erroneous measurements that may occur due to blurriness. As well as blurriness of the image, the mobile device, in use may also prompt the user to check alignment of the mobile device with the card and/or to alter the distance between the digital imaging device and the reference card. When presenting the image to the user for verification, the mobile device may display a warning message, the warning message prompting the user to check one or more errors in the image taken. These errors may include: focus problems (the warning message may ask the user to check that the image is not blurred); alignment problems (the warning message may prompt the user to check that the relative angle between the reference card and the mobile device is less than a particular threshold angle; a non-complete image caused by obstruction of at least part of the lens of the digital imaging device; and/or the reference card being placed too close or too far away from the digital imaging device.

The error may be an angle between the card and the mobile device (i.e. if the picture is taken at a perspective). A threshold may be set for the relative angle such that the mobile device will only capture an image if the relative angle is below the threshold. In this way, unwanted noise that arises from perspective images and that could lead to measurement uncertainty, is reduced.

The user may be prompted to re-take the photo. Alternatively or additionally, defects such as blurriness, alignment and distance-related problems may be detected automatically during processing of the image.

Optionally, if a measurement of some property of the hair is required a calibration process must be provided. Optionally, the calibration process includes an algorithm for extracting features of the one or more calibration markers from the image of the hair fibre captured with the imaging device. The calibration process may also include an algorithm that operates on the captured image using information derived from the marker features to size and/or rotate and or/crop the captured image to advantageously present the part of the captured image containing the hair fibre for subsequent measurements.

In some embodiments additional data relevant to the calibration markings may be independently available to the algorithms for purposes of comparison. For example they may be hard coded values embedded in the on phone application, or advantageously modifiable as part of an application upgrade mechanism using the web.

In some embodiments this data may be independently encoded on the reference card for example using a Quick Response code (QR code) or a bar code extractable from the raw image by known algorithms.

In a further embodiment the QR or bar code may on a separate object for example an FMCG product format and is captured and decoded by the phone app in as a prior step using standard algorithms.

The calibration marker may take the form of a marking which extends along at least a part of the card. It may take the form of a marking which extends around the perimeter of the card at the edge of the card or at a set distance from the edge of the card.

In some embodiments, the marker may take the form of a shape which may contain extra information, for example a logo.

In some embodiments markings may be used to indicate the location of the hair attachment points and may be also be calibration markers.

In some embodiments markings may be used to bind a region on the card, in which the only featured object can be the hair itself when attached. These markings can also be calibration markers.

In some embodiments the size and/or shape of the reference card itself may be used as part of the calibration process instead of or in addition to a calibration marker. The measurements of the reference card could include the height, length or any other measurement of a part the reference card such as distance between diagonally opposing corners.

To extract the calibration markers from the raw images an algorithm may be provided. This algorithm may have two stages: a segmentation procedure that extracts the pixels of the calibration markers from the raw image; and a classification procedure that assigns identity to groups of pixels as being particular markers. This algorithm may make use of prior knowledge as described above. The segmentation procedure refers to segmentation of the calibration markers from the background. For the purposes of this segmentation, the hair fibre itself forms part of the background.

In one possible embodiment the specifically chosen visual colour of the calibration markers may be used as the basis of pixel segmentation and a pre stored digital template (see above) then used to assign marker identity to the pixels and determine the location of particular features on the template, using a matching process.

Measurements of the calibration markers may be used to define a transformation matrix which can be used to create a calibrated version of the raw image with the size of the pixels known in terms of real world physical values (for example in terms of microns).

In one embodiment, the transformation may be arranged such that an output is a calibrated image scaled, rotated and/or cropped with respect to the original such that the only feature visible in the calibrated image is the hair fibre and so that the hair fibre is aligned vertically with the grid of the image pixel array.

Optionally the diameter measurement of the hair fibre may be made using this calibrated image as the input.

Optionally, to generate the diameter measurement, the mobile device is configured to: record the digital image taken by the digital device in a memory of the mobile device; process the recorded image using a segmentation algorithm for extracting one or more calibration markers and/or the reference card boundary; scale the captured image using the extracted calibration data to create a calibrated image with a known relation to actual physical dimensions; and to extract the diameter of the hair from the calibrated image. Optionally, to generate the diameter measurement, the mobile device is further configured to rotate and/or crop the captured image such that the orientation and/or size of the calibrated image of the hair fibre is optimised for subsequent dimensional analysis. Optionally, the mobile device is configured to access a database comprising a list of hair products, each hair product assigned to one or more ranges of hair diameters for which the product is suitable.

Once a hair diameter measurement has been made, the mobile device may be configured to access the database and to generate an output of a recommended hair product for the user based on products in the database which are listed against the measured diameter.

The recommended hair product could be one or more of: shampoo, conditioner, treatment, styling product.

The database may be located on a remote server which is accessed by the mobile device following the diameter measurement. Alternatively, the database may be downloaded and stored in the memory of the mobile device.

According to a second aspect of the present invention, there is provided a reference card for use with a computer program to measure the diameter of a human hair, the reference card including: a hair attachment mechanism to attach the hair to the reference card; and one or more calibration markers.

The reference card of may include an identifier which provides: a website address at which a computer program for use with the reference card can be downloaded; and/or instructions for using the card in combination with the computer program.

The reference card may be provided in combination with a hair product, for example removably attached to the packaging of a hair product.

According to a third aspect, there is provided a computer program for measuring the diameter of a human hair using a mobile device, the computer program configured to carry out the steps of: obtaining an image of a human hair on a reference card, the reference card including a hair attachment mechanism and one or more calibration markers; and converting the image of the hair into a measurement of the diameter of the hair using the one or more calibration markers as a size reference. The computer program may be provided in combination with the reference card.

The computer program may be an app which may be downloaded onto a mobile device. There may be provided a computer program product for measuring the diameter of a human hair using a mobile device, the computer program product tangibly embodied in a non-transitory computer readable medium, the computer program product including instructions being configured to cause a data processing apparatus to:

obtain an image of a human hair on a reference card, the reference card including one or more calibration markers;

convert the image of the hair into a measurement of the diameter of the hair using the one or more calibration markers as a size reference.

Obtaining the image of the human hair on the reference card could include the step of capturing a digital image using the mobile device's own digital imaging device.

According to a fourth aspect, there is provided a method of measuring the diameter of a human hair, the method comprising the steps of: obtaining an image of a human hair attached to a reference card, the reference card including a calibration marker; and converting the image of the hair into a measurement of the diameter of the hair using the calibration marker as a size reference.

The method may further comprise the step of: providing the reference card to which the human hair is attached, the reference card including: a hair attachment mechanism; and a calibration marker.

The method may also comprise the step of attaching the human hair to the reference card using the hair attachment mechanism.

Further optional features of the invention are set out below.

BRIEF DESCRIPTION OF THE DRAWINGS

Embodiments of the invention will now be described by way of example with reference to the accompanying drawings in which:

FIG. 7 shows an example process for identifying the optimal hair fibre boundary.

DETAILED DESCRIPTION AND FURTHER OPTIONAL FEATURES OF THE INVENTION

A system for measuring the diameter of a human hair 50 is described with reference to FIGS. 1 to 3 below.

The system comprises a mobile device 20 and a reference card 10, the reference card comprising a hair attachment mechanism configured to hold the hair 50 onto the card and also a calibration marker 12 on the card which provides a size reference against which the hair can be compared.

Figure 1:
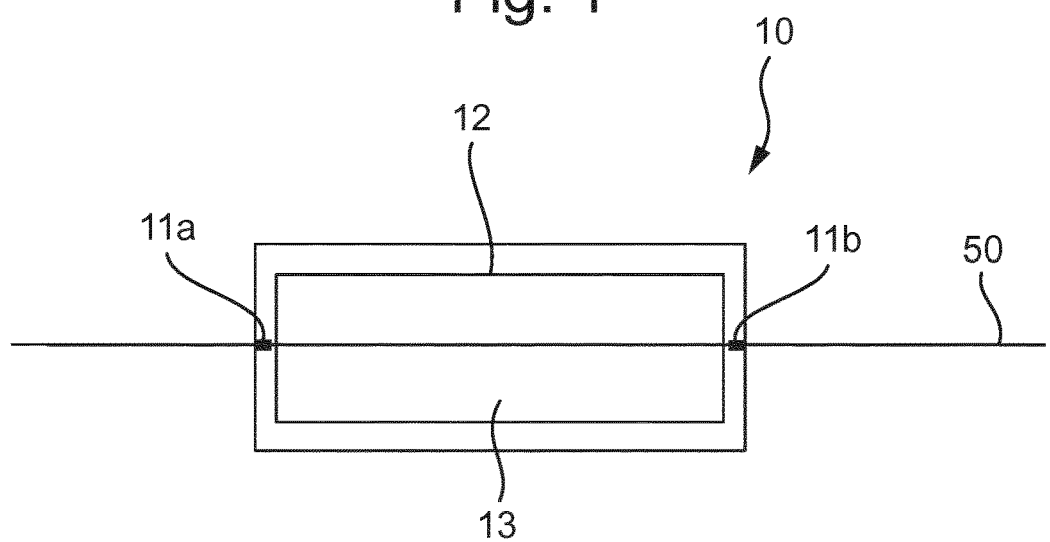
FIG. 1 shows a schematic diagram of a reference card.

The reference card shown in FIG. 1 is rectangular in shape and includes a surface 13 against which the hair should be located before measurement takes place. In the embodiment of FIG. 1, the surface is a light colour such as white in order to maximise contrast between it and dark hairs placed upon it (e.g. brown or black hairs).

The hair attachment mechanism of the reference card shown in FIG. 1 is a pair of connectors, each connector taking the form of a slit in the card which traps a hair placed within it. The first connector forms an attachment point at one end of the card and the second connector forms a second attachment point at an opposite end of the card. By trapping a single hair 20 simultaneously at both attachment points, the hair 50 is held taught along the length of the reference card. By locating the two attachment points at opposing ends of the elongate reference card the area over which the hair is held is maximised which can be beneficial if average diameter measurements are to be taken along the length of the hair.

As well as being opposite, the attachment points are aligned such that when a hair is held taught between the two points it will lie parallel to the elongate axis of the reference card. Where a reference card is to be used with curly hair, it may additionally include an adhesive region (not shown), the adhesive region located on top of the surface 13 in-between the two attachment points. The adhesive region is preferably matt and either transparent or light coloured such that the colour contrast between the surface and the hair is maintained.

The calibration marker 12 of the reference card shown in FIG. 1 takes the form of a line marked onto the surface 13 of the reference card, the line located at a set distance inwardly displaced from the perimeter of the card and, in this embodiment, extending around the entire perimeter of the card. It should be understood that the calibration marker could take the form of any other marker on the card having a specific thickness and/or length and/or distance from the edge of the card.

Figure 2:
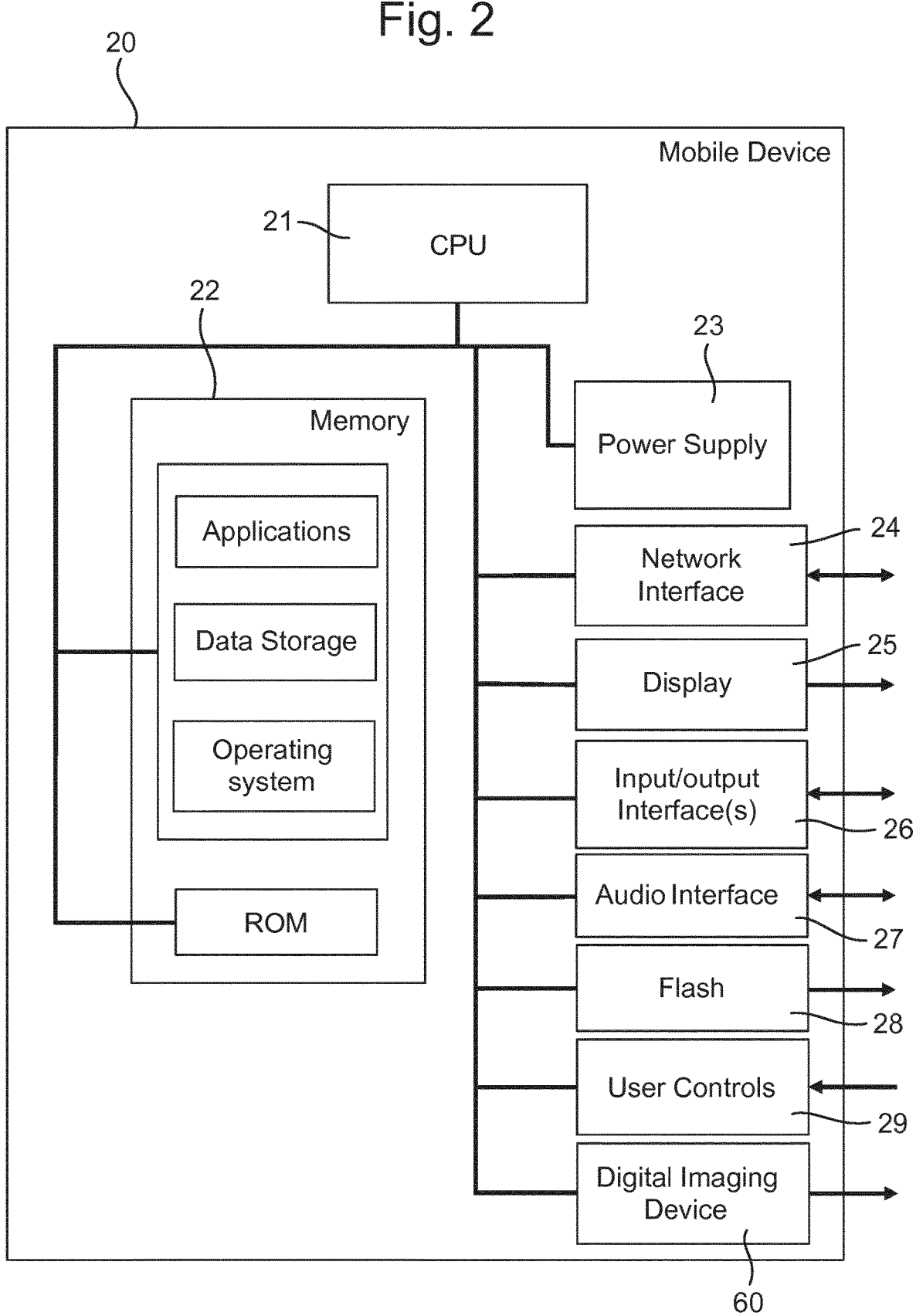
FIG. 2 shows a schematic diagram of a mobile device.

FIG. 2 shows an illustrative embodiment of a mobile device which is suitable for practicing the various aspects and embodiments of the present invention. The mobile device may include all of the components shown but may contain more, or less.

The mobile device 20 includes a digital imaging device 60 such as a digital camera for recording digital photographs. These photographs may then be stored in a data storage section of the memory 22.

The mobile device 20 shown includes a central processing unit (CPU) 21 in communication with a memory 22 and various other components.

These other components of the mobile device 20 shown include a power supply 23, a network interface 24, a display 25, an input/output interface 26, an audio interface 27, a flash 28 and user controls 29.

The power supply 23 provides the power used by the mobile interface and may take the form of a rechargeable battery and/or external power source.

The network interface 24 provides a mechanism for the mobile device to communicate directly or indirectly with any other computing device and includes circuitry configured for use with one or more communication protocols and technologies including but not limited to: GPRS; GSM; TDMA; transmission control protocol/Internet protocol (TCP/IP); CDMA; WCDMA; Wi-Fi; 3G, 4G, Bluetooth or any other wireless communication protocols.

The display 25 may be an LCD (Liquid crystal display), a plasma display or any other suitable electronic display and may be touch sensitive in that it may include a screen configured to receive an input from a human digit or a stylus.

Input/output interface(s) 26 may include one or more ports for outputting information e.g. audio information via headphones, but may also be an input port configured to receive signals including remote control signals.

The audio interface 27 typically includes a speaker which enables the mobile device to output signals and a microphone which enables the mobile device to receive audio signals including voice control inputs for use in controlling applications.

The mobile device 20 shown includes a flash 28 which may be used in conjunction with the digital imaging device to illuminate an object of which a photograph is being taken. User controls 29 may take the form of external buttons or slider which allow a user to control various functions of the mobile device.

An application saved on the device may be configured to interact with the various components of the device such that upon receiving an input from one or more of the user controls, the digital imaging device and is triggered and a digital photograph is taken of an object (such as the hair on the reference card). This image may then be stored in the memory and one or more algorithms may be used to process the stored image.

The computer program described herein may take the form of an application stored in the memory 22.

The mobile device 20 may be configured to exchange information with other computers via a network 40. The network may include the internet and/or one or more local area networks (LANs) or wide area networks (WANs).

Figure 3:
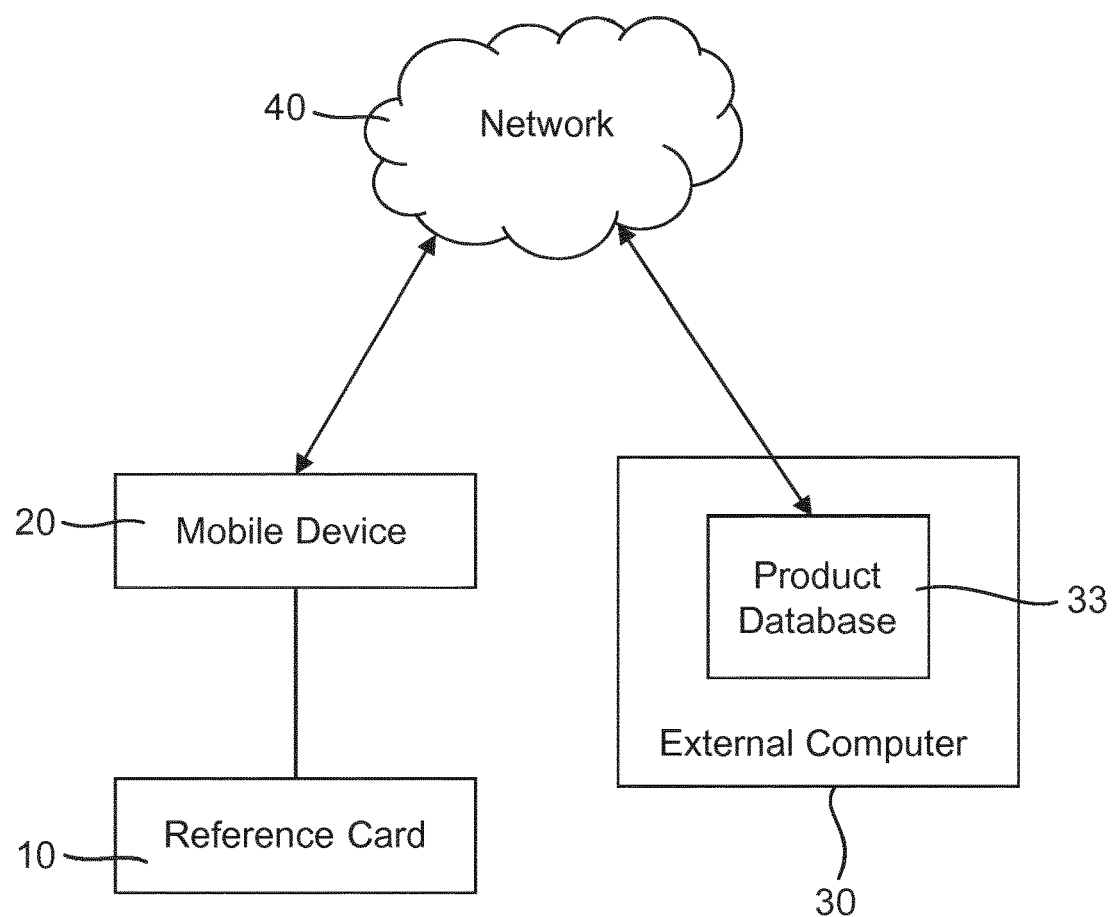
FIG. 3 shows a schematic diagram of a mobile device and reference card in communication with a network.

As shown in FIG. 3, this exchange of information may include accessing a product database 33 on an external computer 30. The product database may include a list of suitable products and an indication of the diameter of hair for which the product is most suitable. This indication could be an upper diameter threshold, a lower diameter threshold, or a range of suitable diameters.

In this way, processed information extracted from an image taken of a user's hair on the reference card 10 can be compared and matched against the indication in the product database. Selection criteria can then be applied to select the most suitable product for the user based on the numerical value or label.

In other embodiments, the product database may be stored within the memory 22 of the mobile device.

It should be understood that information such as the measurements taken and/or product selection can be communicated with external servers via the network 40. For example, the user could share this information with others by posting the information on social media websites.

A method of measuring the diameter of a human hair is described below with reference to FIGS. 4a and 4b, where like reference numerals correspond to features described in relation to FIGS. 1 to 3.

A reference card 10 is provided along with a mobile device 20. The hair 50 to be measured is attached (s1) to the reference card 10 so that the hair lies against the surface 13 of the reference card. Where the reference card includes two attachment points, the hair is attached to a first attachment point (e.g. a slit in the card) and a pulling force is applied to the hair before it is attached at the second attachment point so that the hair is held still in a taught configuration between the two attachment points.

Opposing slits are simple and cost effective attachment points, requiring no additional parts and very little additional manufacturing steps. In addition, whilst the opposing slits are capable of holding the hair taught in a fixed position against the surface 13 of the reference card 10, they are not capable of applying an excessive force to the hair which would damage it and affect the reliability of the diameter measurement.

The remaining steps are carried out by the mobile device, preferably using a mobile application which has been downloaded onto the device. The reference card may include instructions and/or a website link which the user can access using the mobile device to download the application.

An image of the hair on the card is taken (s3) using the digital imaging device 60 of the mobile device. The image must include at least a portion of the calibration marker, the portion being sufficient to image all of a known parameter of the calibration marker (e.g. its width and/or length).

The image may then be stored in the memory 22 before being processed. Alternatively, a previously taken image (taken using the mobile device and stored in the memory 22 or taken using a separate digital imaging device such a stand-alone digital camera and saved to the memory 22) could be accessed for processing.

Image processing includes the step of applying a thresholding algorithm to the image to segment the image into a foreground and a background.

Before carrying out image processing, a verification step may be added which may include displaying the image to the user along with a warning message so that the user can themselves perform a visual quality check of the image before processing takes place.

The image is calibrated (s4) with respect to either the calibration marker or to the size of the card itself, for example it's length or width. The calibration marker is of a known size and/or position (e.g. its width, its length, or the distance from the marker to the edge of the reference card). This means that the size of each pixel can be calculated based on how many pixels correspond to this known parameter.

The diameter measurement is then extracted (s5) from the processed image. An edge detection algorithm (such as a Sobel operation) is applied to measure the diameter (thickness) of the hair transverse to its longitudinal axis. From this pixel measurement, the actual measurement is calculated using the size of each pixel extracted from the calibration step.

Multiple measurements may be taken along the length of the hair and averaged to give a more accurate result. Outlier measurements which are more than or less than a given multiple of the standard deviation (e.g. 1.2 times the standard deviation) are removed before the average is taken to further improve accuracy.

Once a value for the diameter has been obtained this is compared to a product database 33 which may be saved within the memory of the mobile device itself or may hosted on an external computer or server and accessed via a network.

Where the product database is located externally, it may be more easily maintained and kept up to date to remove old products, add new products etc.

Each product listed in the database will be assigned a specific range in diameters. It is this assigned range which is matched (s6) with the actual diameter measurement (averaged or otherwise). The mobile device will extract recommended products based on the closest match between the measured hair diameter and the diameter ranges of the respective products.

Products may be split into product categories e.g. shampoo, conditioner treatments and styling products, and a product may be recommended (s7) from each category. Extraction (s5) of the diameter of a hair from an image may require a number of operations to be carried out on the image. An example of the hair measurement extraction process (s5) is shown in more detail in FIGS. 4a and 4b.

The quality of the image is checked (s51), for example by applying a Laplacian filter to check for blurriness. If the filter detects blurriness, an error message can be generated which instructs the user to re-take the photograph.

Once the image quality has been checked, the image is cropped (s52) to a pre-defined window smaller than the size of the total image. Not only does this serve to reduce the number of pixels to be processed but it also removes outer regions including areas containing the calibration marker that may lead to spurious results.

The image is then converted to grayscale (s53). In addition, further algorithms may be applied to increase the contrast and or reduce the noise (s54) of the pixels present. An algorithm is then applied (500) to the image to identify the hair fibre boundaries and then estimate the hair fibre diameter this algorithm consists of a series of steps:

A 1D gradient filter is applied to the greyscale image (s55). If the hair fibre is aligned vertically (as a result of the calibration process) cutting across the rows of pixels then the 1D gradient filter is applied row by row. Alternatively if the hair fibre is aligned along a row of pixels then the 1D gradient filter is applied column by column.

In some embodiments, the gradient filter may include the standard estimate of the first derivative, based upon the differences in intensity between neighbouring pixels.

Other embodiments may include alternative implementations of the gradient filter. For example the Canny, Roberts, Prewitt and Sobel filters. Depending on the quality of the imaging process and subsequent noise characteristics one or other method may be preferred. Sobel operators have been found to be advantageously less prone to noise. Assuming that the hair fibre is aligned vertically, then taking each row of the cropped image in turn (s56) the gradient filter output is analysed.

In each row the positions of the minimum and maximum value of the gradient filtered image is identified (s57) and these point together with their two neighbouring points are used to construct two parabolas. This is shown in more detail in FIG. 7.

The left boundary of the hair is given by the location of minimum of the left hand parabola. The right hand boundary of the hair is given by the location of the maximum of the right hand parabola (s58). The left hand parabola can be seen in FIG. 7.

The width of the hair fibre is then calculated (s59) by subtracting the position of the left hand boundary from the position of the right hand boundary.

A mean measurement may then be calculated. This mean measurement may be a mean over a subsection of the rows or a mean calculated over all of the rows. Further statistics for example the diameter variance or standard deviation may also be calculated. One advantage of the above approach is that it allows a sub pixel estimation of the location of the hair fibre boundary, and so improves the estimate of diameter over methods that seek to directly segment out the hair fibre before attempting the measurement, since the hair fibre diameter in that case can only be estimated to the nearest whole number of pixels in width.

The row-by-row approach assumes that in the image taken, the hair is attached to the reference card vertically, i.e. each row goes across the hair fibre. If the hair is attached horizontally, the image could be analysed column-by-column, rather than row-by-row.

Figure 4A:
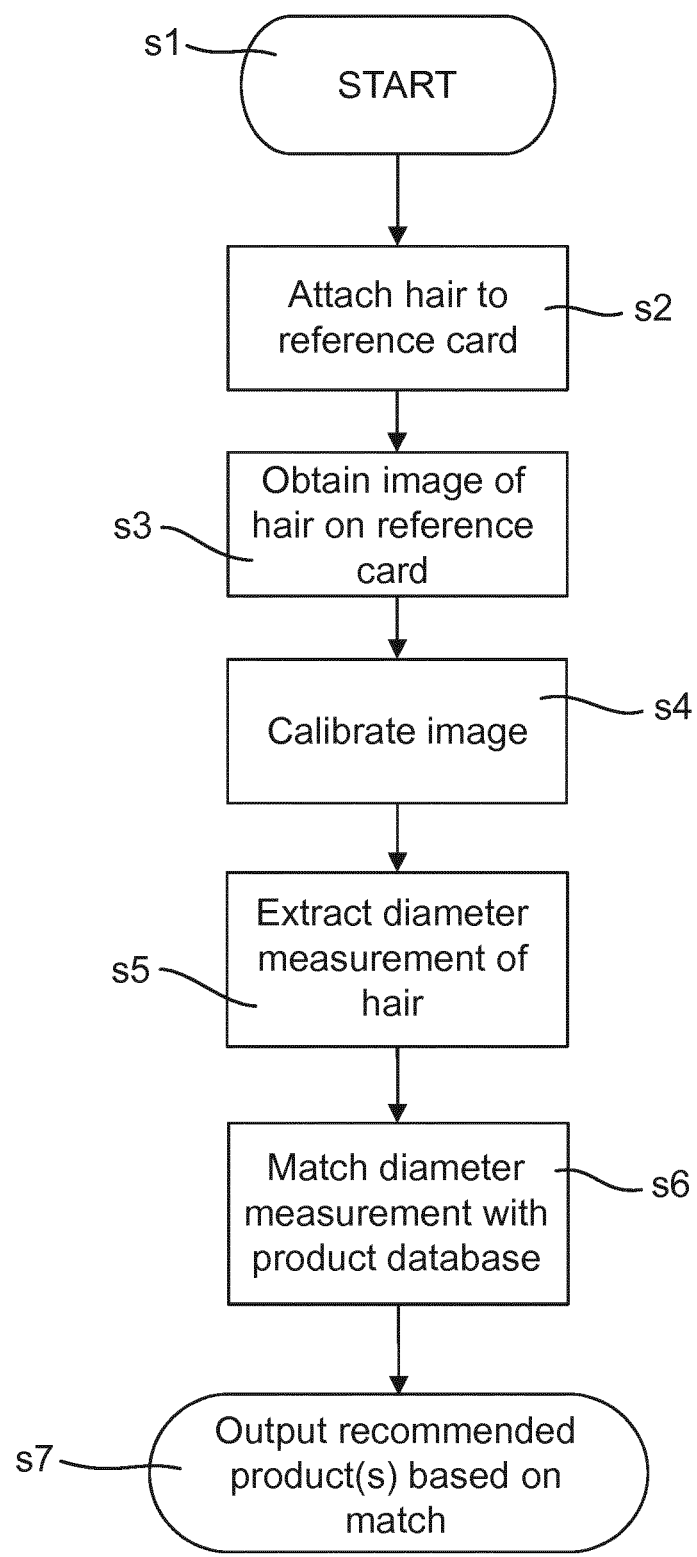
FIGS. 4*a* and 4*b* show a process for measuring the diameter of a human hair.
Figure 4B:
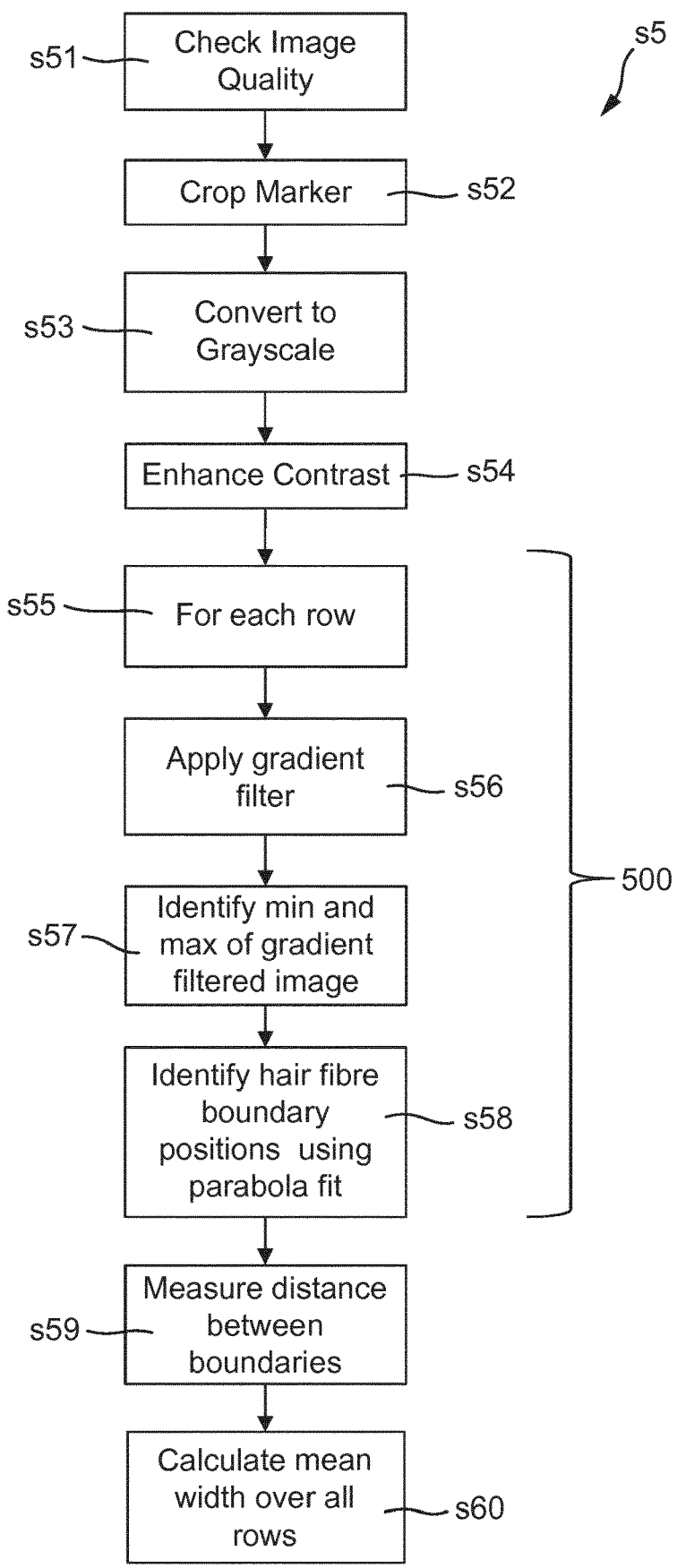

Although FIGS. 4a and 4b illustrate one example, it would be understood that one or more of the steps may be omitted and that the steps may be carried out in a different order to that shown.

The entire measurement process could be carried out in real time.

Figure 5:
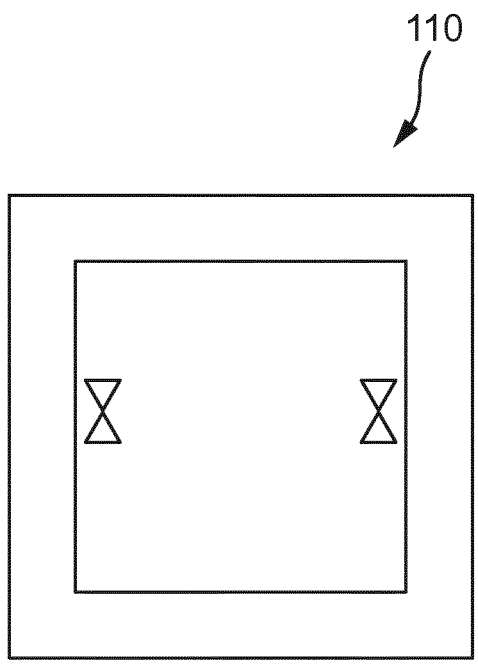
FIG. 5 shows a schematic diagram of an example of a reference card.

An example of an alternative reference card 110 is shown in FIG. 5. In this embodiment, the reference card is square and contains triangular markings as well as a boarder, the width of the boarder being at least $\frac{1}{8}^{th}$ of the total width of the card. The hair attachment means are not visible in the figure.

Figure 6A:
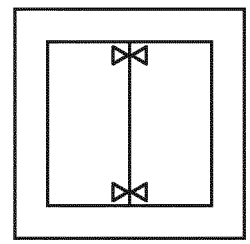
FIGS. 6*a*-6*e* show various steps carried out on the mobile device to process the image taken before a measurement of the diameter of the hair is made.
Figure 6B:
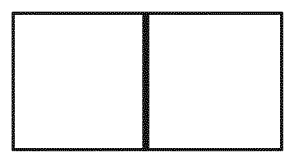
Figure 6C:
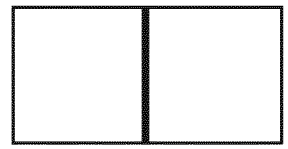

FIGS. 6a-6e depict various steps carried out on the mobile device to process the image of taken before a measurement of the diameter of the hair is made. FIG. 6a depicts an image, taken by the mobile device, of a hair on the reference card 110. FIG. 6b shows an example of the image once it has been cropped. FIG. 6c shows an example of the cropped image once it has been converted to grayscale.

Figure 6D:
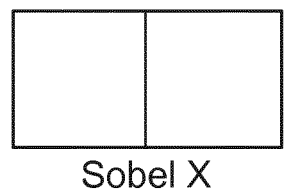
Figure 6E:
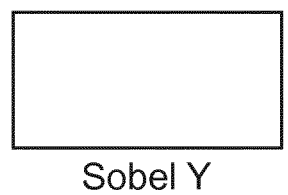

FIGS. 6d and 6e show Sobel X and Sobel Y outputs respectively. In this example, the Sobel X output would then be analysed row-by-row and the turning points in the resulting cross sections would be used to determine the width of the hair, for example using the parabola method described above;

In any one of the embodiments described herein, the process of determining hair diameter may include the additional step of removing outlier measurements, such as those greater than one standard deviation from the mean. This advantageously improves robustness against erroneous measurements caused by noise.

As well as taking averages over different points along the length of a hair, the mobile device may be configured to capture more than one image over a "session". The width measurements generated at each reading within this session may then be averaged. Diameter measurements may be saved to the device and/or may be shared, e.g. via email, SMS or social media. Where images are saved, additional data may be saved alongside the image. This data may include calibration information such as the number of microns per pixel. It may also include more details relating to the actual diameter. For example, it may include the minimum hair diameter measured; the maximum hair diameter measured; the median hair diameter measured; the mean hair diameter measured; the standard deviation; the variance; the minimum outlier count; the maximum outlier count; and details about what filters were applied to the image. The information will also include a label/tag.

The mobile device may also be configured to generate a summary of past sample results. These could be assigned to one or more users and so could be used to compare hair diameters of different users, or different hair diameter measurements of the same user over time.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A system for measuring the diameter of a human hair, the system comprising:
    a mobile device; and
    a reference card including a hair attachment mechanism; the mobile device configured to convert an image of a human hair attached to the reference card by the attachment mechanism into a measurement of the diameter of the human hair, using the size of the reference card itself and/or the size of a calibration marker on a surface of the reference card as a size reference.

2. The system of claim 1, wherein the mobile device comprises a digital imaging device for capturing the image of the human hair attached to the reference card.

3. The system of claim 1, wherein the hair attachment mechanism takes the form of a first attachment point at one end of the card for receiving one end of the hair and a second attachment point at the opposite end of the card for receiving the other end of the hair.

4. The system of claim 3, wherein one or more of the attachment points is a slit in the card.

5. The system of claim 1 wherein a surface of the reference card includes an adhesive region.

6. The system of claim 1, wherein the reference card has a matt surface.

7. The system of claim 1 wherein to generate the diameter measurement, the mobile device is configured to:
    record the digital image taken by the digital device in a memory of the mobile device;
    process the recorded image using an segmentation algorithm to extract one or more calibration markers and/or the reference card boundary;
    scale the captured image using the extracted calibration data to create a calibrated image with a known relation to actual physical dimensions; and
    extract the diameter of the hair from the calibrated image.

8. The system of claim 7 wherein to generate the diameter measurement, the mobile device is further configured to rotate and/or crop the captured image such that the orientation and/or size of the calibrated image of the hair fibre is optimised for subsequent dimensional analysis.

9. The system of claim 1, wherein the mobile device is configured to access a database comprising a list of hair products, each hair product assigned one or more ranges of hair diameters for which the product is suitable.

10. The system of claim 9, wherein, once a hair diameter measurement has been made, the mobile device is configured to access the database and to generate an output of a recommended hair product for the user based on products in the database which are listed against the measured diameter.

11. The system of claim 1, wherein the mobile device is configured to present the image taken by the digital imaging device to the user for quality verification before processing the image.

12. A method of measuring the diameter of a human hair, the method comprising the steps of:
    obtaining an image of a human hair attached to a reference card, the reference card including one or more calibration markers; and
    converting the image of the hair into a measurement of the diameter of the hair using the one or more calibration markers as a size reference.

13. A method of measuring the diameter of a human hair, the method comprising the steps of:
    providing a reference card, the reference card including a hair attachment mechanism;
    attaching a human hair to the reference card using the hair attachment mechanism;
    obtaining an image of the human hair attached to the reference card, the reference card including one or more calibration markers; and
    converting the image of the hair into a measurement of the diameter of the hair using the one or more calibration markers as a size reference.

* * * * *